United States Patent
Stray (10) Patent No.: US 10,954,428 B2
(45) Date of Patent: Mar. 23, 2021

(54) ALKOXYPHENYL CARBOXYLIC ACID TRACERS

(71) Applicant: RESTRACK AS, Kjeller (NO)

(72) Inventor: Helge Stray, Kjeller (NO)

(73) Assignee: RESTRACK AS, Kjeller (NO)

( * ) Notice: Subject to any disclaimer, the term of this patent is extended or adjusted under 35 U.S.C. 154(b) by 629 days.

(21) Appl. No.: 15/548,804

(22) PCT Filed: Feb. 5, 2016

(86) PCT No.: PCT/EP2016/052573
§ 371 (c)(1),
(2) Date: Aug. 4, 2017

(87) PCT Pub. No.: WO2016/124778
PCT Pub. Date: Aug. 11, 2016

(65) Prior Publication Data
US 2018/0030331 A1    Feb. 1, 2018

(30) Foreign Application Priority Data

Feb. 6, 2015   (NO) .................................. 20150181

(51) Int. Cl.
*C09K 8/58*     (2006.01)
*E21B 47/11*    (2012.01)
(Continued)

(52) U.S. Cl.
CPC .............. *C09K 8/58* (2013.01); *C07C 65/21* (2013.01); *E21B 47/11* (2020.05); *G01N 30/72* (2013.01); *G01N 30/8679* (2013.01)

(58) Field of Classification Search
CPC ....... C09K 8/58; C07C 65/21; E21B 47/1015; G01N 30/72; G01N 30/8679
See application file for complete search history.

(56) References Cited

U.S. PATENT DOCUMENTS 3,086,990 A * 4/1963 Wilkins .................. C07C 59/64
                                              562/470
3,508,875 A    4/1970 Sandiford
(Continued)

FOREIGN PATENT DOCUMENTS

EP        1774137 B1   2/2008
WO      02/095189 A1  11/2002
WO     2006/004426 A1  1/2006

OTHER PUBLICATIONS

EPA. Method 615: The Determination of Chlorinated Herbicides in Municipal and Industrial Wastewater, 1992, <https://www.epa.gov/sites/production/files/2015-10/documents/method_615_1992.pdf>. (Year: 1992).*

(Continued)

*Primary Examiner* — Crystal J Miller
(74) *Attorney, Agent, or Firm* — Banner & Witcoff, Ltd.

(57) ABSTRACT

The invention provides for the use of at least one aromatic acid compound of formula i), or a salt thereof, as a water tracer; wherein n is 0, 1 or 2, $R_1$ to $R_5$ are each independently H, alkyl or alkoxy and wherein at least one of $R_1$ to $R_5$ is alkoxy. The invention further provides for a method of monitoring the flow of water within a structure having an inflow point and an outflow point, where the method comprises; a) introducing at least a one tracer of formula i) into (Continued)

said inflow point; b) collecting fluid at said outflow point; and c) measuring the presence and/or concentration of said tracer in said fluid collected at said outflow point over time.

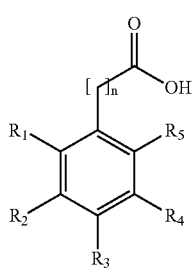

i)

15 Claims, 2 Drawing Sheets (51) Int. Cl.
C07C 65/21 (2006.01)
G01N 30/72 (2006.01)
G01N 30/86 (2006.01)

(56) References Cited

U.S. PATENT DOCUMENTS

| | | | |
|---|---|---|---|
| 3,508,876 A * | 4/1970 | Polly | E21B 43/20 436/27 |
| 3,537,992 A | 11/1970 | Kolaian | |
| 5,168,927 A * | 12/1992 | Stegemeier | E21B 47/1015 166/252.6 |
| 5,246,860 A * | 9/1993 | Hutchins | G01N 33/241 116/250 |
| 2006/0144588 A1 | 7/2006 | Ferguson et al. | |
| 2010/0016181 A1 | 1/2010 | Stray | |
| 2011/0260051 A1* | 10/2011 | Preudhomme | E21B 43/16 250/282 |
| 2015/0323515 A1* | 11/2015 | Rule | G01N 33/241 166/250.12 |
| 2016/0209391 A1* | 7/2016 | Zhang | G01N 33/2847 |

OTHER PUBLICATIONS

Xue, Haoran, et al. "Design, Construction and Characterization of a Set of Biosensors for Aromatic Compounds." ACS Synthetic Biology, vol. 3, No. 12, Dec. 2014. pp. 1011-1014 <https://pubs.acs.org/doi/pdf/10.1021/sb500023f>. Accessed Oct. 26, 2020. (Year: 2014).*
May 2, 2016—(WO) International Search Report and Written Opinion—App PCT/EP2016/052573.
Bath, A., Drilling Fluid Tracers-Review and update of industry experience and issues for Rwmd site characterisation programme, Apr. 2011, Itellsci LTd, Project 1007.23.
Ali, E., Chatzichristos, C., Aurdal, T, Muller, J., 2000. Tracer simulation to improve the reservoir model in the Snorre Field. Paper SPE 64796 presented at the SPE International Oil and Gas Conference and Exhibition in China, Beijing.
Bjornstad, T., 1994. Recent and current oil fields tracer development for interwell application. Second Tracer Workshop. University of Texas at Austin, Austin, TX, pp. 101-113.
Bjornstad, T., Haugen, O.B., Hundere, I.A., 1994. Dynamic behavior of radiolabelled water tracer candidates for chalk reservoirs. J. Pet. Sci. Eng. 10, 223-238.
Chrysikopoulos, C.V., 1993. Artificial tracers for geothermal reservoir studies. Environ. Geol. 22, 60-70. Du, Y., Guan, L., 2005. Interwell tracer tests: lessons learned from past field studies. Paper SPE 93140 Presented at the 2005 Asia Pacific Oil and Gas Conference and Exhibition. Jakarta, Indonesia, 9p.
Dugstad, O., Aurdal, T., Galdiga C., Hundere, I., Torgersen, H.J., 1999. Application of tracers to monitor fluid flow in the Snorre fields: a field study. Paper SPE 25376 Presented at the 1999 SPE Annual Technical Conference and Exhibition. Houston, TX, 10p.
Dugstad Ø., Well-to-well tracer tests, Chapter 6 (pp. 651-683), in Petroleum engineering handbook, vol. 5—Reservoir Engineering and petrophysics. E.D. Holstein (ed.), SPE, Richardson, TX, USA, 2007.
Galdiga, C., 1998. Development of analytical methods for non-radioactive fluorinated tracer compounds in reservoir fluids in petroleum industry. Dissertation for the Degree of Doctor Scientiarum. Department of Chemistry, University of Oslo, Oslo, Norway, pp. 49.
Galdiga, C.U., Greibrokk, T., 1998. Ultra-trace determination of fluorinated aromatic carboxylic acids in aqueous reservoir fluids using solid-phase extraction in combination with gas chromatography-mass spectrometry. J. Chromatogr. A 793, 297-306.
Galdiga, C.U., Greibrokk, T., 1998. Trace analysis of fluorinated aromatic carboxylic acids in aqueous reservoir fluids by HPLC. J. Liq. Chromatogr. Relat. Technol. 21, 855-868.
Galdiga, C.U., Greibrokk, T., 1998. Ultra-trace determination of fluorinated aromatic carboxylic acids in aqueous reservoir fluids by solid-phase extraction in combination with negative ion chemical ionisation mass spectrometry after derivatisation with pentafluorobenzyl bromide. J. Anal. Chem. 361, 797-802.
Hernandez, C., Alvarez, C., Saman, A., De Jongh, A., Audemard, N., 2002. Monitoring WAG pilot at VLE field, Maracaibo Lake, by perfluorocarbon and fluorined benzoic acids tracers. Paper SPE 75259 Presented at the SPE/DOE Improved Oil Recovery Symposium. Tulsa, OK, 9p.
Hirtz, P.N., Kunzman, R.J., Broaddus, M.L, Barbitta, J.A., 2001. Developments in tracer flow testing for geothermal production engineering. Geothermics 30, 727-745.
Huseby, O., Valestrand, R., Naevdal, G., Sagen, J., 2009. Natural and conventional tracers for improving reservoir moduls in EnKF approach. Paper SPE 121190 Presented at the 2009 SPE EuroPEC/EAGE Annual Conference and Exhibition. Amsterdam, the Netherlands, 22p.
Meza, E., Garcia, F., Munoz, N., Reyes, C., Amador, A., 2007. Optimization of tracers test design—practical applications. Paper SPE 108660 Presented at the 2007 International Oil Conference and Exhibition in Mexico. Veracruz, Mexico, 7p.
Prosvimov M.: "Maximizing Recovery: Reservoirs tracers in Ekofisk, Norway". Poster presented at SPE's ATW on Tracer Technology, Dubai, UAE Sep. 8-10, 2014.
Rose, P.E., Benoit, W.R., Kilbourn, P.M., 2001. The application of the polyaromatic sulfonates as tracers in geothermal reservoirs. Geothermics 30, 617-640.
Rose, P.E., McPherson, P.A., 1997. New fluorescent tracers for use in geothermal reservoirs. Geotherm. Resour. Counc. Trans. 21, 249-252.
Sanjuan, B., Pinault, J.-L., Rose, P., Gérard, A., Brach, M., Braibant, G., Crouzet, C., Foucher, J.-C., Gautier, A., Touzelet, S., 2006. Tracer testing of the geothermal heat exchanger at Soultz-sous-Forêts (France) between 2000 and 2005. Geothermics 35, 622-653.
Adams, M.C., Moore, J.N., Fabry, L.G., Ahn, J.-H., 1992, Thermal stabilities of aromatic acids as geothermal tracers. Geothermics 21, 323-339.
Seaman, J.C., Bertsch, P.M.., Wilson, M., Singer, J., Majs, F., Aburime, S.A., 2007. Tracer migration in a radially divergent flow field: longitudinal dispersivity and anionic tracer retardation. Vadose Zone J. 6, 373-386.
Serres-Piole C., Preud'homme H., Moradi-Tehrani N., Allanic C., Jullia H., Lobinski R., 2012.: Water tracers in oilfield applications : Guidelines. Journal of Petroleum Science and Engineering vol. 98-99, pp. 22-39.
Zemel B., Tracers in the Oil Field, Developments in Petroleum Science, 43, Elsevier, New York, 1994.

* cited by examiner

ALKOXYPHENYL CARBOXYLIC ACID TRACERS

The present application is a U.S. National Phase of International Application No. PCT/EP2016/052573, filed on Feb. 5, 2016, designating the United States of America, and claims priority to Norwegian Patent Application No. 20150181, filed Feb. 6, 2015. This application claims priority to and the benefit of the above-identified applications, each of which is fully incorporated by reference herein.

FIELD OF THE INVENTION

The present invention relates to tracers for use in monitoring the flow of water in petroleum reservoirs, as well as other areas where tracer technology is applied. In particular, the invention relates to water tracers having a low environmental impact.

BACKGROUND OF THE INVENTION

In the oil industry, where water is co-produced with oil and/or gas, sustainable operations requires re-injection of produced water to preserve scarce water resources and prevent pollution. As the tracers will be re-injected with water, this water re-injection limits or prohibits re-use of tracers and thus leads to an increasing demand for new and unique water tracers. Furthermore, environmental concerns render many of the existing tracers less than ideal due to their isotopic or chemical composition.

Tracers are inert chemical or radioactive compounds that are used to label and track fluids. In oil field applications they can be used to monitor wells and production equipment, as well as fluid movement in the reservoir [1-27]. In the reservoir, tracers can be used to monitor single well operations, or in inter-well tracer tests to evaluate fluid movement between injectors and producers. A general review of tracers applied in petroleum reservoirs is given by Zemel (1994) [27] and a review of inter-well tracer testing can be found in Dugstad (2007) [7].

In the past, tracers applied in the petroleum industry were usually radioactive, but with the development of chemical tracer technology the last two decades, chemical tracers have largely replaced radioactive tracers. Typical chemical tracers are fluorinated benzoic acids for water (Galdiga et al. [8-11]), or perfluorocarbons for gas (Dugstad et al. [6]). Chemical tracers have obvious advantages for handling and disposal as well as avoiding radioactive contamination of the environment.

When analysing the suitability of tracers for oil reservoirs, several important characteristics should be fulfilled. A tracer has to be sufficiently thermally stable at relevant reservoir temperatures, it should be substantially chemically and biologically stable under reservoir conditions and sorption on the relevant rock surfaces should be negligible. Tracers must also be adequately stable during sample storage, have the necessary analytical sensitivity, be as environmentally acceptable as possible and be unique in the reservoir environment. If the objective of a tracer test is to monitor transport of a single phase (e.g. the water tracers presented here), an additional constraint is that partitioning between fluid phases must not occur to any significant extent.

Chemical tracer testing has been applied in a broad range of inter-well tracer testing (IWTT) applications and is now established and proven as an efficient technology to obtain information on well-to-well communication, heterogeneities and fluid dynamics.

During such tests, tracers are used to label injected fluids from specific injection wells. The tracers are then subsequently used to trace the fluids as they move through the reservoir together with the injection phase. One of the appealing features of IWTT is that at the first tracer breakthrough in a producer, immediate information on the injector-producer communication is given. In some cases tracers may be injected into specific reservoir zones, to reduce ambiguities in interpretation (cf. Dugstad, 2007 [7]).

Fluorinated benzoic acids (FBAs) were introduced for use as tracers in petroleum and geothermal reservoirs in the 1990s and have, since then, been among the most frequently applied chemical tracers for monitoring subterranean fluids [1-13]. The oil industry has chosen to focus on fluorinated benzoic acids because of their chemical and biological stability, low toxicity, good flooding properties and high detectability. One explanation for the stability of these tracers the carbon-fluorine bond, which is the shortest, and thus strongest and most stable, carbon-halide bond (Serres-Piole et al. [25]). About 20 different molecules of FBA are available and commonly used as water tracers in oil reservoirs. These tracers can be detected at concentrations in the parts-per-trillion (PPT) range, using modern analytical instrumentation.

The need for unique tracers is evident, because compounds present naturally or previously added to oil reservoirs will interfere with tracer signals recorded at producers. This introduces detrimental ambiguities in the interpretation, as the origin of the tracer fluid and the time taken for passage to the production point cannot be uniquely identified. Interference by previously used tracers is particularly severe in cases when produced water is re-injected, either to preserve scarce water resources or to avoid pollution of the environment.

There is therefore a continuous demand for development of new water tracers for oil field applications. The need for new unique tracers also increases because oil companies tend to monitor their water injection projects more extensively than previous practice (e.g. Prosvirnov et al., 2014).

In addition to the FBAs, a range of chemical compounds have been proposed for use as water tracers in oil reservoirs (see Serres-Piole et al. [25] for an overview). Unfortunately several of the tracers proposed for oil reservoirs are not well suited, due to interference with reservoir rock surfaces (e.g. fluorescent dyes), biodegradation (e.g. methyl benzoic acids) or insufficient thermal stability (e.g. fluorinated phenyl acetic acids). Moreover, any tracer must be detectable at low levels in the produced water. The reason for this is that small tracer amounts should be injected to avoid or minimise any influence on the physical properties of the reservoir fluids, to minimize environmental impact and reduce costs. An additional constraining factor in development of new tracers is the ambition to reduce the use of halogenated organic compounds due to the hazards of introducing such compounds into the environment. For this reason, even the existing FBA tracers may become difficult to use in the future.

The present inventors have now established that certain alkoxylated aromatic acid compounds provide many or all of the attributes of effective tracers. Such compounds may be stable in the reservoir environment, may cause little or no interaction with the rock of the reservoir and/or may be detectable at low levels in produced water.

SUMMARY OF THE INVENTION

In a first aspect, the present invention provides the use of at least one aromatic acid compound of formula i) (or a salt thereof) as a water tracer;

i)

wherein n is 0, 1 or 2, $R_1$ to $R_5$ are each indenpendently H, alkyl or alkoxy and wherein at least one of $R_1$ to $R_5$ is alkoxy. Where present, alkyl groups will preferably be ethyl or methyl but alkyl groups will preferably be absent. Preferred alkoxy groups include C1 to C4 alkoxy groups such as methoxy, ethoxy, n-propoxy and isopropoxy. Most preferred alkoxy groups are methoxy and ethoxy. Generally, one to four of groups $R_1$ to $R_5$ will be hydrogen. At least one of $R_1$ to $R_5$ will be alkoxy (such as methoxy or ethoxy). Preferably 1 to 4 of $R_1$ to $R_5$ will be alkoxy (such as methoxy or ethoxy), more preferably 1, 2 or 3 and most preferably one or two of $R_1$ to $R_5$ will be alkoxy (such as methoxy or ethoxy).

The number n in formula i) represents the number of methylene groups between the aromatic moiety and the carboxylic acid moiety. This number n in formula i) will be 0, 1 or 2, preferably 0 or 1. Thus the compounds of formula 1 are preferably benzoic acid compounds (n=0), substituted with $R_1$ to $R_5$ as described in any embodiment herein, or are phenyl acetic acid compounds (n=1), substituted with $R_1$ to $R_5$ as described in any embodiment herein.

Typically compounds of formula i) will be used as tracers in monitoring the flow of water within a structure, such as a subterranean reservoir.

Any of the compounds (e.g. of formula i), formula ii) or any of formulae B1-B15 or P1-P15) as described herein in any aspect of the invention may be used as a salt. Any salt may be used, but evidently this will preferably be a water-soluble salt. Preferably the cation will be selected to avoid unnecessary toxicity or environmental impact. Suitable cations include metal ions such as alkali metal ions or alkaline earth metal ions. Organic cations such as ammonium ions may also be used. Thus, corresponding salts such as alkali metal salts, alkaline earth metal salts and salts of organic cations such as ammonium salts fall within the scope of formula i) and of all aspects of the present invention.

In second embodiment, the present invention thus provides for a method of monitoring the flow of water within a structure comprising an inflow point, and an outflow point in at least partial fluid communication with said inflow point (used herein synonymously with "input point"), said method comprising;

a) introducing at least a one tracer having a structure of formula i) into said inflow point;

b) collecting fluid at said outflow point; and c) measuring the presence and/or concentration of said tracer in said fluid collected at said outflow point over time.

The method may additionally comprise the step of;

d) relating the presence and/or concentration of said tracer in said fluid collected at said outflow point over time to the nature of said structure.

In all aspects of the present invention, the structure to be monitored may be a subterranean structure such as a reservoir. This may be a water or hydrocarbon reservoir such as an oil or gas reservoir. In the case of a subterranean reservoir, the inflow point will typically be a well or bore, such as an injection well. Similarly, in the case of a subterranean reservoir, the outflow point may be a well such as a production well. The structure may comprise one or more inflow points. The structure may also comprise one or more outflow points.

Other structures that may be monitored in various aspects of the present invention include geothermal structures (e.g. reservoirs), ground-water and aqueous fluids in industrial processes.

The compounds of formula i) (e.g. methoxy or ethoxy compounds) presented here may have less environmental impact than previously developed tracers (e.g. fluorinated compounds) and should be preferred even in juvenile oil fields, where re-injection of previous tracers are not yet an issue.

DETAILED DESCRIPTION OF THE INVENTION

This invention relates to application of compounds of formula i) (e.g. benzoic acids and phenylacetic acids) substituted with alkoxy (e.g. methoxy or ethoxy) groups. These compounds have been found to have excellent properties in respect to chemical stability, flooding properties and detectability. The compounds do not seem to be present in produced water samples at significant levels, and natural occurring organic compounds present in produced water has not been found to interfere with analysis of the tracers when modern analytical techniques are used.

Preferred compounds of formula i) include those of formulae iia) and iib) below:

iia)

iib)

In formulae iia) and iib), each of $R_1$ to $R_5$ may be any of those groups indicated above in respect of formula i). In particular, one to four, preferably two or three of groups $R_1$ to $R_5$ may independently be methoxy or ethoxy. The remaining groups $R_1$ to $R_5$ will preferably be hydrogen.

Examples of compounds useful in all aspects of the present invention include benzoic acids of formulae B1 to B15:

Junwee Chemical Co., Ltd., China or Sigma-Aldrich) and/or prepared by methods known in the art.

Further examples of compounds useful in all aspects of the present invention include phenyl acetic acid compounds of the following formulae P1 to P15:

wherein in each of B1 to B15, each $R_6$ group is independently an alkyl group, such as a C1 to C5, or C1 to C3 alkyl group. Preferably each $R_6$ is independently a methyl or ethyl group. Compounds of formula i) and of each of the formulae indicated herein may be sourced commercially (e.g. from the wherein in each of P1 to P15, each $R_6$ group is independently an alkyl group, such as a C1 to C5, or C1 to C3 alkyl group. Preferably each $R_6$ is independently a methyl or ethyl group.

Highly preferred compounds for use in the various aspects of the present invention include: 3,4-dimethoxybenzoic acid (3,4-DMBA), 3,4-dimethoxyphenylacetic acid (3,4-DMPAA), 3,4-dimethoxyphenylacetic acid (3,4-DMOPAA) and 3,4,5-trimethoxybenzoic acid (3,4,5-TMOBA). Other compounds of interest include 3,5-dimethoxybenzoic acid, 3-ethoxy-4-methoxybenzoic acid, 2,4-Dimethoxybenzoic acid, 2,6-Dimethoxybenzoic acid, 2,4,6-trimethoxybenzoic acid, 2,4-dimethoxyphenylacetic acid, 2,3,4-trimethoxyphenylacetic acid, (2-ethoxy-5-methoxyphenyl)acetic acid, (3,5-dimethoxyphenyl)acetic acid, and (2,5-dimethoxyphenyl)acetic acid.

In all aspects of the present invention, the tracers used will generally be selected as being highly soluble in water and essentially insoluble in oil. This property is represented by the oil/water partition coefficient and is a well-studied property in the art. For the tracers described herein, the partition coefficient is generally less than $10^{-2}$, e.g. less than $10^{-3}$, such as less than $10^{-4}$, less than $10^{-5}$ or less than $10^{-6}$ (between seawater and oil at 80° C.).

Preferably, the compounds of formula i) (and the preferred compounds as indicated herein) are stable in water at concentration levels typical in water samples from oil reservoirs (typical concentration level is 50 ppt to 100 ppb) for at least 4 weeks at reservoir temperatures. Preferably such compounds are stable for at least 6 weeks, preferably at least 8 weeks under such conditions. Preferably, this stability will be exhibited at temperatures of at least 80° C., more preferably at least 100° C., most preferably at temperatures of at least 150° C. "Stable" in this context may be taken as having a concentration of tracer compound within 20% of the starting concentration as measured by GC-MS, more preferably within 10%.

A further key feature of the compounds used in the various aspects of the present invention is their high detectability. Specifically, the compounds of formula i) (and the preferred compounds as indicated herein) are preferably detectable by GC-MS down to a concentration of 500 ppt (parts per trillion) or lower. Preferably this detection limit will be 100 ppt or lower, more preferably 50 ppt or lower. It is possible for the detection limit to be still lower, such as 1 ppt or 100 ppq.

Detection of the compounds of the present invention may be achieved by many methods which are well known in the relevant art. For example, Gas Chromatography (GC) or High Performance Liquid Chromatography (HPLC) are typical separation methods and Electrophoresis may also be suitable. The compounds will present characteristic retention times on suitable media, such as normal or reversed-phase columns and will be detectable by methods including optical detection (such as UV absorption) and mass-spectroscopic detection (MS or MS(MS) detection).

A still further important feature of the compounds used in the various aspects of the present invention is their relatively low environmental impact. Specifically, the compounds of formula i) (and the preferred compounds as indicated herein) are preferably classified as "red" or better (e.g. "red" or "yellow") according to the HOCNF (Harmonized Offshore Chemical Notification Format for chemicals released to the North Sea) testing criteria. In one preferred embodiment, the compounds used in the various aspects of the present invention are classified as "yellow" or better.

A yet further feature of the compounds used in the various aspects of the present invention is their low reaction with and sorption onto materials typically found in oil fields such as rock, particularly limestone and/or sandstone. Specifically, the compounds of formula i) (and the preferred compounds as indicated herein) will typically be stable in the presence of sandstone and/or limestone for at least a month, more preferably at least two months under aqueous conditions at temperatures corresponding to oil reservoir temperatures. Preferably, this stability will be exhibited at temperatures of at least 80° C., more preferably at least 100° C., most preferably at temperatures of at least 150° C. "Stable" in this context may be taken as having a concentration of tracer compound within 20% of the starting concentration as measured by GC-MS, more preferably within 10%.

In the methods of the present invention, any tracer described herein may be used to analyse the flow of water within a structure such as a hydrocarbon reservoir. Evidently more than one tracer may be used and in such cases, the first tracer will be a tracer as described herein and second and subsequent tracers may be tracers as described herein, may be other water tracers (such as the commonly used fluorobenzoic acid tracers) or may be "partitioning" tracers. Partitioning tracers are also well known in the art any may be used in combination with water tracers (so-called "passive" tracers) such as those described herein in methods to analyse properties such as residual oil saturation in a reservoir. Such tracers and methods are described, for example in WO2014/096459, the disclosure of which is hereby incorporated herein by reference.

The methods of the present invention may thus be solely for monitoring water flow, or may be for monitoring or determining properties such as the level of hydrocarbon (e.g. residual oil saturation) in the structure (e.g. reservoir).

Evidently, the methods of the present invention are not limited to introducing tracers from a single inflow point. Where a structure, such as a reservoir, has more than one inflow point, a tracer may be introduced at multiple points. In such an embodiment, the same tracer may be used at each inflow point, but more preferably a different tracer will be used at each inflow point so that information on the fluid flow between each inflow point and at least one outflow point may be determined. Calculation or computer modelling may be employed to determine the relative flows between various points on the structure from the presence, absence and/or concentration of the one or more tracers in the outflowing water over time. Where a plurality of tracers is used, each may be a tracer of formula (i) or the tracers described herein may be used in combination with other known tracers, such as fluorobenzoic acids.

Similarly, the method of the present invention may be used more than once at a single inflow point. Where water from the structure is re-injected, such as by recycling produced water in an oil reservoir, it is preferable that a different tracer of formula i) is used on each occasion.

EXAMPLES

Example 1—Detectability

Figure 1:
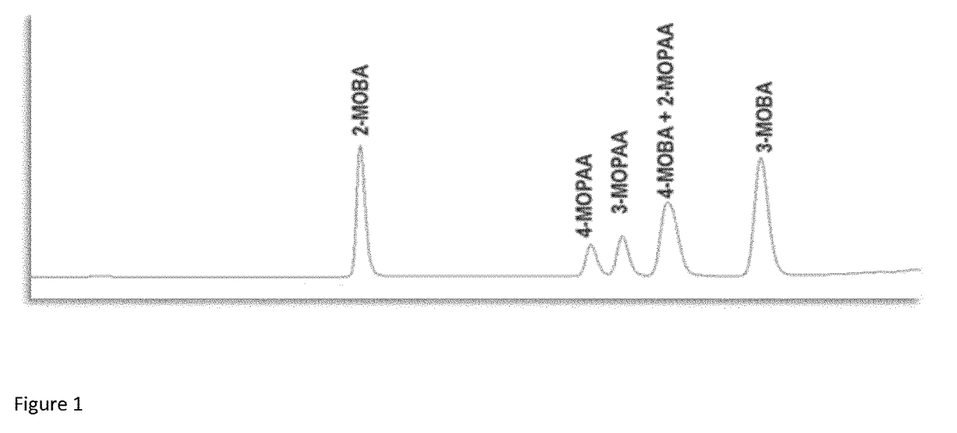
FIG. 1 shows a plot of a chromatograms of 3 isomers of monomethoxybenzoic acids and 3 isomers of monomethoxyphenylacetic acids.

FIG. 1 shows that typical examples of the new tracer candidates can be separated and individually detected with high performance liquid chromatography using UV detection (HPLC-UV). The chromatogram of 3 isomers of monomethoxybenzoic acids and 3 isomers of monomethoxyphenylacetic acids are shown.

Example 2—Stability

Figure 2:
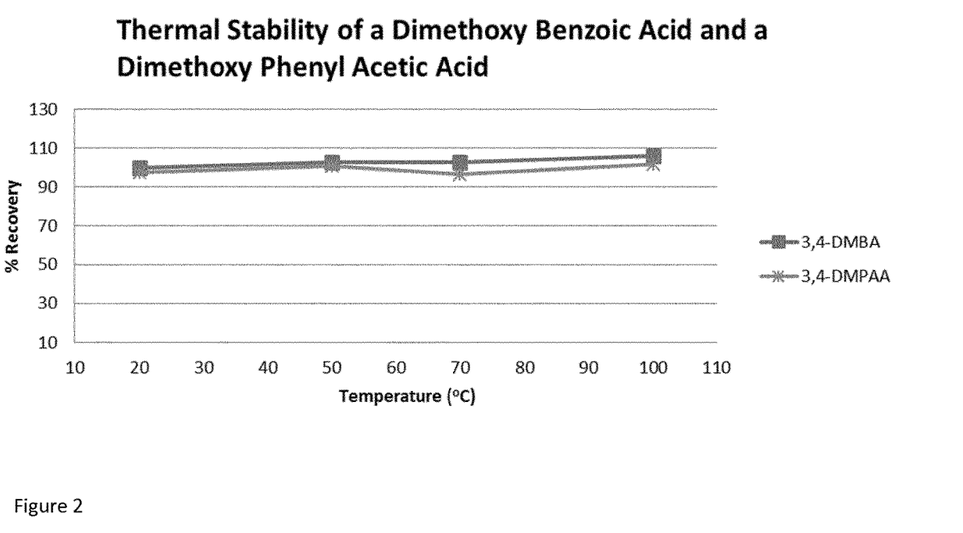
FIG. 2 is a plot of the recovery of 3,4-dimethoxybenzoic acid (3,4-DMBA) and 3,4-dimethoxyphenylacetic acid (3,4-DMPAA) at temperatures from 20 to 100° C. in reservoir like matrices.

Compounds of methoxy and ethoxy benzoic acids and phenylacetic acids were tested for thermal stability up to 150° C. The compounds were found to be thermally stable at least up to 100° C. The recovery data shown in FIG. 2 confirm this statement. The tracer candidates shown are: 2-methoxybenzoic acid (2-MOBA), 4-methoxybenzoic acid (4-MOBA) and 3-methoxybenzoic acid (3-MOBA).

Example 3—Flooding

Figure 3:
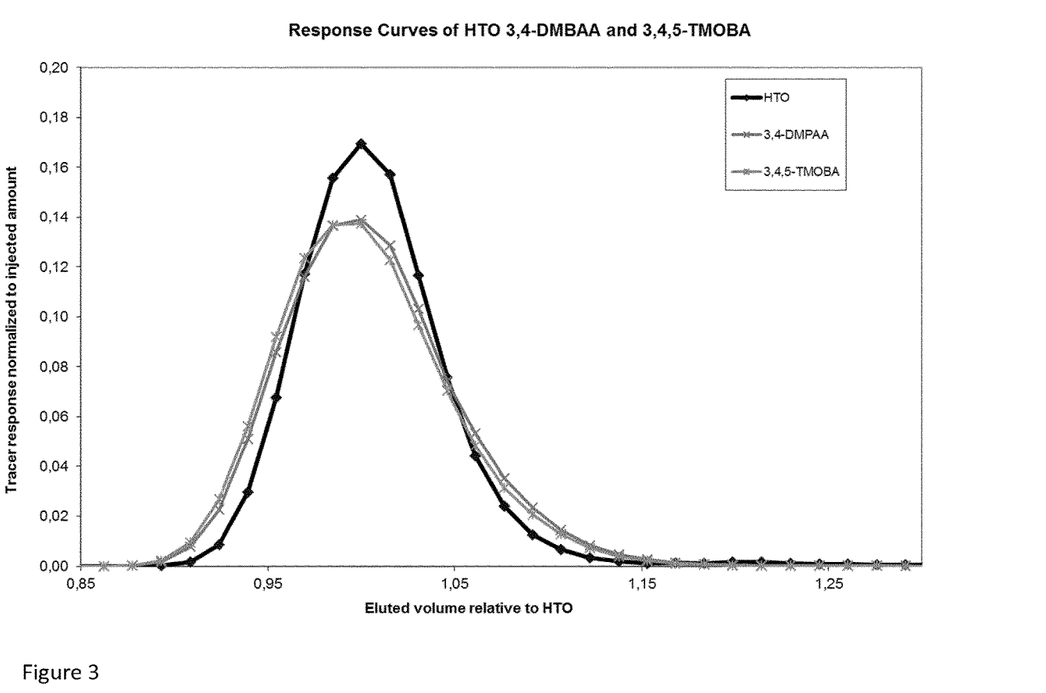
FIG. 3 is a plot of the responses of 3,4-dimethoxyphenylacetic acid (3,4-DMOPAA) and 3,4,5-trimethoxybenzoic acid (3,4,5-TMOBA) compared to the response of HTO (the ideal water tracer) in a flooding experiment at typical reservoir conditions
Figure 4:
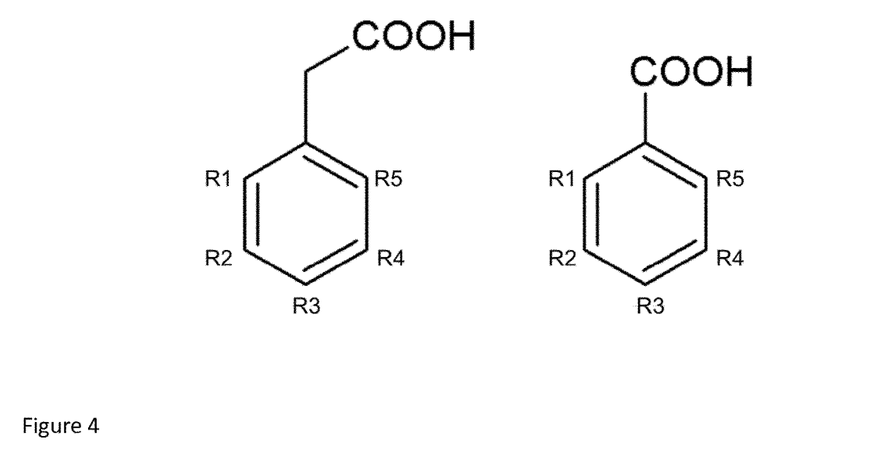
FIG. 4 shows the structural formula of phenylacetic and benzoic acid with substituents R1 to R5.

The tracer candidates described in Example 2 were also tested for flooding properties. Laboratory experiments performed at reservoir conditions (sand-packed column, 11 mm ID, 200 cm long, at residual oil saturation, flooded with artificial sea water at 120 bar, 100° C.) confirmed that they all have flooding properties similar to tritiated water (HTO). FIG. 3 shows the results of a selected tracer candidate.

REFERENCES

1. Ali, E., Chatzichristos, C., Aurdal, T, Muller, J., 2000. Tracer simulation to improve the reservoir model in the Snorre Field. Paper SPE 64796 presented at the SPE International Oil and Gas Conference and Exhibition in China, Beijing.
2. Bjornstad, T., 1994. Recent and current oil fields tracer development for interwell application. Second Tracer Workshop. University of Texas at Austin, Austin, Tex., pp. 101-113.
3. Bjornstad, T., Haugen, O. B., Hundere, I. A., 1994. Dynamic behavior of radiolabelled water tracer candidates for chalk reservoirs. J. Pet. Sci. Eng. 10, 223-238.
4. Chrysikopoulos, C. V., 1993. Artificial tracers for geothermal reservoir studies. Environ. Geol. 22, 60-70.
5. Du, Y., Guan, L., 2005. Interwell tracer tests: lessons learned from past field studies. Paper SPE 93140 Presented at the 2005 Asia Pacific Oil and Gas Conference and Exhibition. Jakarta, Indonesia, 9p.
6. Dugstad, O., Aurdal, T., Galdiga C., Hundere, I., Torgersen, H. J., 1999. Application of tracers to monitor fluid flow in the Snorre fields: a field study. Paper SPE 25376 Presented at the 1999 SPE Annual Technical Conference and Exhibition. Houston, Tex., 10p.
7. Dugstad Ø., Well-to-well tracer tests, Chapter 6 (pp 651-683), In Petroleum engineering handbook, Vol 5-Reservoir engineering and petrophysics. E. D. Holstein (ed.), SPE, Richardson, Tex., USA, 2007.
8. Galdiga, C., 1998. Development of analytical methods for non-radioactive fluorinated tracer compounds in reservoir fluids in petroleum industry. Dissertation for the Degree of Doctor Scientiarum. Department of Chemistry, University of Oslo, Oslo, Norway, pp. 49.
9. Galdiga, C. U., Greibrokk, T., 1998. Ultra-trace determination of fluorinated aromatic carboxylic acids in aqueous reservoir fluids using solid-phase extraction in combination with gas chromatography-mass spectrometry. J. Chromatogr. A 793, 297-306.
10. Galdiga, C. U., Greibrokk, T., 1998. Trace analysis of fluorinated aromatic carboxylic acids in aqueous reservoir fluids by HPLC. J. Liq. Chromatogr. Relat. Technol. 21, 855-868.
11. Galdiga, C. U., Greibrokk, T., 1998. Ultra-trace determination of fluorinated aromatic carboxylic acids in aqueous reservoir fluids by solid-phase extraction in combination with negative ion chemical ionisation mass spectrometry after derivatisation with pentafluorobenzyl bromide. J. Anal. Chem. 361, 797-802.
12. Hampton, T. Shaw, D., Broacha, E., Malone, S., 2001. Method of Determining the Extend of Recovery of Materials Injected into Oil Wells. Publication no. WO02/095189 A1.
13. Hernandez, C., Alvarez, C., Saman, A., De Jongh, A., Audemard, N., 2002. Monitoring WAG pilot at VLE field, Maracaibo Lake, by perfluorocarbon and fluorined benzoic acids tracers. Paper SPE 75259 Presented at the SPE/DOE Improved Oil Recovery Symposium. Tulsa, Okla., 9p.
14. Hirtz, P. N., Kunzman, R. J., Broaddus, M. L., Barbitta, J. A., 2001. Developments in tracer flow testing for geothermal production engineering. Geothermics 30, 727-745.
15. Huseby, O., Valestrand, R., Naevdal, G., Sagen, J., 2009. Natural and conventional tracers for improving reservoir moduls in EnKF approach. Paper SPE 121190 Presented at the 2009 SPE EUROPEC/EAGE Annual Conference and Exhibition. Amsterdam, The Netherlands, 22p.
16. Hutchins, R. D., Saunders, D. L., 1992. Tracer Chemicals for Use in Monitoring Subterranean Fluids. Publication no. 5 246 860.
17. Meza, E., Garcia, F., Munoz, N., Reyes, C., Amador, A., 2007. Optimisation of tracers test design—practical applications. Paper SPE 108660 Presented at the 2007 International Oil Conference and Exhibition in Mexico. Veracruz, Mexico, 7p.
18. Prosvirnov M.: "Maximizing Recovery: Reservoirs tracers in Ekofisk, Norway". Poster presented at SPE's ATW on Tracer Technology, Dubai, UAE 8-10 Sep. 2014.
19. Rose, P. E., Benoit, W. R., Kilbourn, P. M., 2001. The application of the polyaromatic sulfonates as tracers in geothermal reservoirs. Geothermics 30, 617-640.

20. Rose, P. E., McPherson, P. A., 1997. New fluorescent tracers for use in geothermal reservoirs. Geotherm. Resour. Counc. Trans. 21, 249-252.
21. Sanjuan, B., Pinault, J.-L., Rose, P., Gérard, A., Brach, M., Braibant, G., Crouzet, C., Foucher, J.-C., Gautier, A., Touzelet, S., 2006. Tracer testing of the geothermal heat exchanger at Soultz-sous-Forêts (France) between 2000 and 2005. Geothermics 35, 622-653.
22. Stray, H., Dugstad, O., Hassfjell, S., 2005. System for Delivery of a Tracer in Field Transport Systems and Use Thereof. Publication no. WO 2006/004426/EP 1 774 137 B1.
23. Adams, M. C., Moore, J. N., Fabry, L. G., Ahn, J.-H., 1992, Thermal stabilities of aromatic acids as geothermal tracers. Geothermics 21, 323-339.
24. Seaman, J. C., Bertsch, P. M., Wilson, M., Singer, J., Majs, F., Aburime, S. A., 2007. Tracer migration in a radially divergent flow field: longitudinal dispersivity and anionic tracer retardation. Vadose Zone J. 6, 373-386.
25. Serres-Piole C., Preud'homme H., Moradi-Tehrani N., Allanic C., Jullia H., Lobinski R., 2012.: Water tracers in oilfield applications: Guidelines. Journal of Petroleum Science and Engineering vol. 98-99, pp. 22-39.
26. Zemel B., Tracers in the Oil Field (Elsevier, NY, 1994)

The invention claimed is:

1. A method of monitoring the flow of water within an oil and/or a gas reservoir, a geothermal reservoir or a groundwater reservoir comprising an inflow point, and an outflow point in at least partial fluid communication with said inflow point, characterised in that said method comprises:
    a) introducing at least a one tracer into said inflow point;
    b) collecting fluid at said outflow point; and
    c) measuring the presence and/or concentration of said tracer in said fluid collected at said outflow point over time;
    wherein said tracer is an aromatic acid compound, or a salt thereof, characterised in that the aromatic acid compound is a compound of formula i;

i)

and wherein n is 0, 1 or 2, $R_1$ to $R_5$ are each independently H, alkyl or alkoxy and wherein at least one of $R_1$ to $R_5$ is alkoxy.

2. The method of claim 1 additionally comprising the step of:
    d) relating the presence and/or concentration of said tracer in said fluid collected at said outflow point over time to the nature of said structure.

3. The method of claim 1 wherein said inflow point is an injection well and said outflow point is a production well.

4. The method of claim 1 wherein step c) is carried out by a method selected from high performance liquid chromatography and gas chromatography, each having a detection method selected from mass spectrometry (MS) and tandem mass spectrometry (MS/MS).

5. The method of claim 1 wherein said tracer is used in combination with a second, partitioning, tracer to determine the saturation of hydrocarbon in said structure.

6. The method of claim 1 wherein each of $R_1$ to $R_5$ is hydrogen or alkoxy and at least one of $R_1$ to $R_5$ is alkoxy.

7. The method of claim 1 wherein each alkoxy group is independently a C1 to C4 alkoxy group.

8. The method of claim 1 wherein each alkoxy group is independently methoxy or ethoxy.

9. The method of claim 1 wherein one to three of $R_1$ to $R_5$ is independently alkoxy.

10. The method of claim 1 wherein the compound of formula i) is a compound of formula iia) or iib) or a salt thereof:

iia)

iib)

wherein each of groups $R_1$ to $R_5$ is as defined in claim 1.

11. The method of claim 10 wherein two or three of groups $R_1$ to $R_5$ are independently methoxy or ethoxy and the remaining groups $R_1$ to $R_5$ are hydrogen.

12. The method of claim 1 wherein the compound of formula i) is a benzoic acid compound of formula B1 to B15:

-continued wherein each group $R_6$ is independently a C1 to C3 alkyl group.

13. The method of claim 12 wherein each group R6 is independently a methyl or ethyl group.

14. The method of claim 1 wherein the compound of formula i) is a phenyl acetic acid compound of formula P1 to P15:

wherein each group $R_6$ is independently a C1 to C3 alkyl group.

15. The method of claim 14 wherein each group R6 is independently a methyl or ethyl group.

* * * * *